United States Patent
Bocz et al.

(10) Patent No.: US 12,201,763 B2
(45) Date of Patent: Jan. 21, 2025

(54) BLOOD TREATMENT DEVICE WITH AUTOMATIC AIR REMOVAL

(71) Applicant: B. Braun Avitum AG, Melsungen (DE)

(72) Inventors: Máté Bocz, Budapest (HU); István Golarits, Budapest (HU); Botond Tényi, Budapest (HU)

(73) Assignee: B. Braun Avitum AG, Melsungen (DE)

( * ) Notice: Subject to any disclaimer, the term of this patent is extended or adjusted under 35 U.S.C. 154(b) by 1154 days.

(21) Appl. No.: 17/032,070

(22) Filed: Sep. 25, 2020

(65) Prior Publication Data

US 2021/0093773 A1 Apr. 1, 2021

(30) Foreign Application Priority Data

Sep. 27, 2019 (DE) ...................... 10 2019 126 189.9

(51) Int. Cl.
  *A61M 1/36* (2006.01)
  *A61M 1/26* (2006.01)

(52) U.S. Cl.
  CPC .......... *A61M 1/3626* (2013.01); *A61M 1/267* (2014.02); *A61M 1/3638* (2014.02);
  (Continued)

(58) Field of Classification Search
  CPC .............. A61M 1/3626; A61M 1/3627; A61M 1/3628; A61M 1/3629; A61M 1/3643;
  (Continued)

(56) References Cited

U.S. PATENT DOCUMENTS

| | | |
|---|---|---|
| 5,863,421 A | 1/1999 | Peter, Jr. et al. |
| 6,044,691 A | 4/2000 | Kenley et al. |

(Continued)

FOREIGN PATENT DOCUMENTS

| | | |
|---|---|---|
| DE | 19655228 B4 | 9/2008 |
| DE | 112014001324 T5 | 1/2016 |

(Continued)

OTHER PUBLICATIONS

Extended European Search Report received in Application No. 20197901.0-1113 dated Mar. 1, 2021, with translation, 11 pages.

(Continued)

*Primary Examiner* — Philip R Wiest
(74) *Attorney, Agent, or Firm* — Christopher A. Rothe; CM Law

(57) ABSTRACT

A blood treatment device includes an extracorporeal blood circuit, a dialyzer and a dialysis fluid circuit. The extracorporeal blood circuit has an arterial portion, a venous portion, an air detector configured to monitor whether air is present in the venous portion, at least one blood pump configured to pump blood through the extracorporeal blood circuit, a venous hose clamp configured to selectively clamp or release the venous portion, a user interface, and a control unit. When the control unit receives information from the air detector that there is air in the venous portion, the control unit is configured to stop the blood pump, close the venous hose clamp, raise an alarm, and display on the user interface instructions for removing air in the venous portion and displaying status reports about the removal of air, and carry out automatic removal of air from the venous portion on a user-initiated basis.

11 Claims, 2 Drawing Sheets

Figure 1:
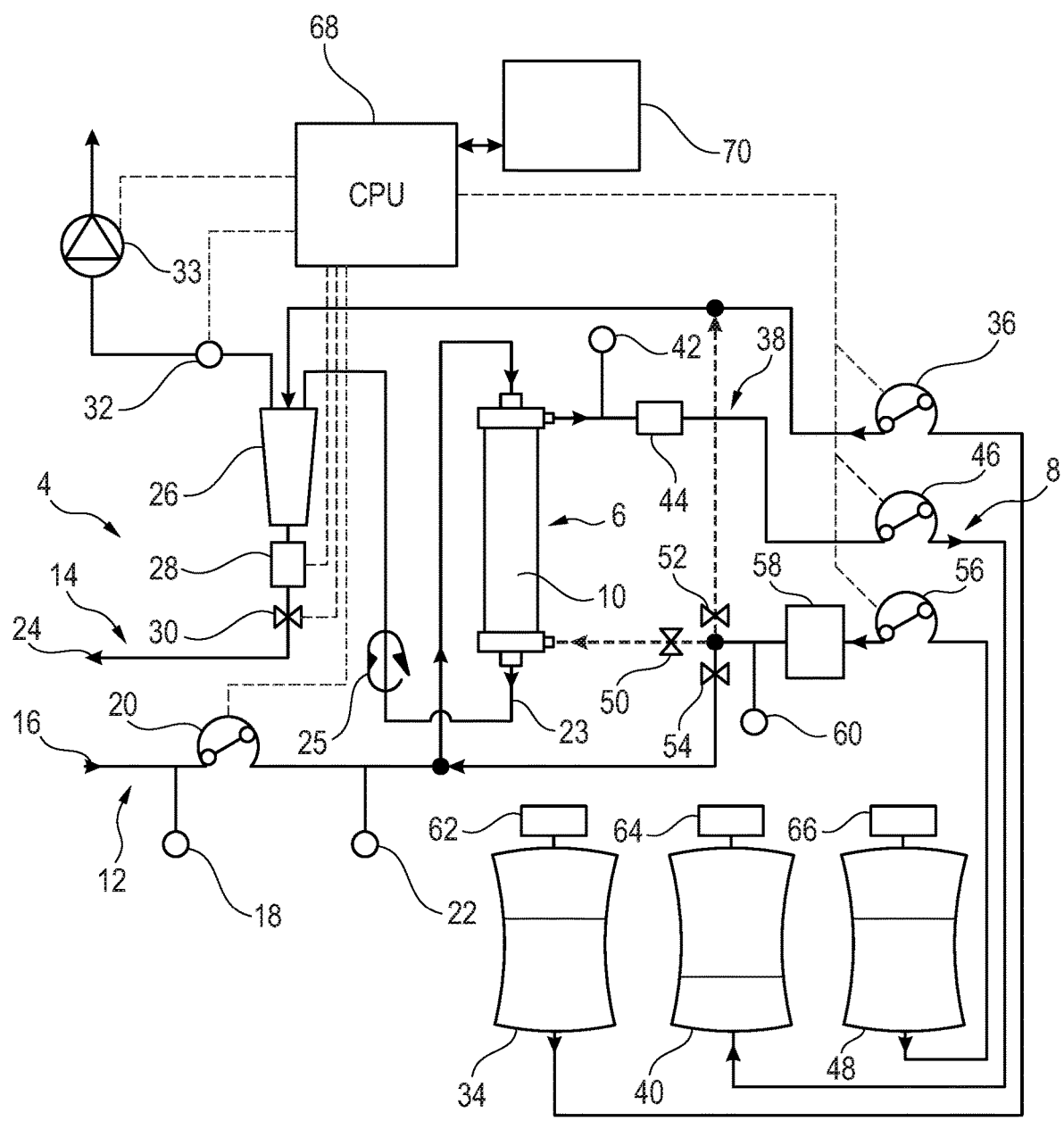

(52) U.S. Cl.
CPC . *A61M 2205/18* (2013.01); *A61M 2205/3331* (2013.01); *A61M 2205/505* (2013.01)

(58) Field of Classification Search
CPC ...... A61M 1/267; A61M 1/284; A61M 1/288; A61M 2205/3331; A61M 2205/505
See application file for complete search history.

(56) References Cited

U.S. PATENT DOCUMENTS

| | | | |
|---|---|---|---|
| 9,320,843 | B2 | 4/2016 | Gagel et al. |
| 9,795,731 | B2 | 10/2017 | Kelly et al. |
| 2009/0088675 | A1 | 4/2009 | Kelly et al. |
| 2010/0191164 | A1 | 7/2010 | Sasaki et al. |
| 2011/0163030 | A1 | 7/2011 | Weaver et al. |
| 2014/0338756 | A1* | 11/2014 | Kelly .................. A61M 1/1601 137/15.01 |
| 2017/0224899 | A1 | 8/2017 | Wojke et al. |
| 2019/0001046 | A1* | 1/2019 | Arrizza ............... A61M 1/3627 |
| 2020/0254167 | A1* | 8/2020 | Rohde .................. A61M 1/284 |

FOREIGN PATENT DOCUMENTS

| | | |
|---|---|---|
| WO | 9301858 A1 | 2/1993 |
| WO | 2007008448 A2 | 1/2007 |
| WO | 2014090370 A1 | 6/2014 |
| WO | 2016020061 A2 | 2/2016 |
| WO | 2017106356 A1 | 6/2017 |
| WO | 2019027688 A1 | 2/2019 |

OTHER PUBLICATIONS

German Search Report received in Application No. 10 2019 126 189.9 dated May 27, 2020, 13 pages.
Artis, Operator's Manual, SP00200, 8.09, Sep. 2012, 924 pages.
Artis, Operator's Manual, 6992739, 7.05, Nov. 2009, 1092 pages.
Dialog + Dialysis Machine, Instructions for Use SW 9.1x, B|Braun, May 2016, 284 pages.
The Ottawa Hospital, Nephrology Program Department Policies and Procedures, Hemodialysis—Section 10—Gambro Artis—Neph 10-04, Oct. 2011, 5 pages.

* cited by examiner

BLOOD TREATMENT DEVICE WITH AUTOMATIC AIR REMOVAL

CROSS-REFERENCE TO RELATED APPLICATION(S)

This application claims priority under 35 U.S.C. § 119 to German Application No. 10 2019 126 189.9, filed Sep. 27, 2019, the contents of which is incorporated by reference herein in its entirety.

FIELD

The present disclosure relates to a blood treatment device, in particular a dialysis device, for use in (continuous) blood treatment/dialysis therapies, in particular renal replacement therapies, comprising: an extracorporeal blood circuit, a dialyzer and a dialysis fluid circuit, wherein the extracorporeal blood circuit and the dialysis fluid circuit are separated from each other via a (semipermeable) membrane provided in the dialyzer, via which blood can be filtered (using a dialysis fluid), and the extracorporeal blood circuit comprises an arterial portion upstream of the dialyzer and a venous portion downstream of the dialyzer; an air detector arranged in the venous portion and configured to constantly/permanently/continuously monitor the venous portion to determine whether air is present in the venous portion; a plurality of pumps, including at least one blood pump, which is a pump in the arterial portion and which is configured to pump blood through the extracorporeal blood circuit; a venous hose clamp, which is a hose clamp in the venous portion and which is configured to selectively clamp or release the venous portion; and a user interface comprising a touch screen display.

BACKGROUND

Blood treatment devices are already known from the prior art. For example, WO 93/01858 A discloses a blood treatment device with a control unit. If air is detected in a venous portion of the extracorporeal blood circuit, the control unit raises an alarm and automatically closes a venous hose clamp. The air is removed from the venous portion by inserting a sterile syringe into a vent line of a filter of an air collection chamber, then opening a valve in the vent line and sucking out the air.

Another document, U.S. Pat. No. 9,795,731 B2, also discloses a blood treatment device with a control unit. According to this document, air is removed from a venous portion of an extracorporeal blood circuit by means of a blood pump.

If there is air in the venous portion of an extracorporeal blood circuit, this is generally a dangerous situation for a patient. It is known from the prior art that air present in the venous portion of the extracorporeal blood circuit has to be removed and that a blood treatment therapy should only be continued after removal. However, the prior art basically has the disadvantage that air removal from the venous portion is relatively complicated and cumbersome and therefore not user-friendly.

SUMMARY

It is therefore the object of the present disclosure to avoid or at least reduce the disadvantages of the prior art. In particular, the blood treatment device is to be configured in such a way that air can be removed from a venous portion of the extracorporeal blood circuit in a simple and user-friendly manner.

This object is solved in a generic blood treatment device in that it has a control unit that is configured, when it receives information from the air detector that there is air in the venous portion, to stop the blood pump, to close the venous hose clamp, to raise an alarm and to display a venous air removal window on the display, which displays instructions for a user for removing the air in the venous portion and displays status reports on the removal of the air, and to perform an automatic removal of the air from the venous portion on a user-initiated basis.

According to the present disclosure, the simplification and user-friendliness is achieved in particular by the combination of steps carried out automatically by the control unit and steps to be carried out manually by a user according to the disclosure. According to the disclosure, the control unit automatically initiates steps which are carried out if there is air in the venous portion. According to the disclosure, the control unit stops the blood pump, closes the venous hose clamp, raises the alarm, and shows the venous air removal window on the display. The special indication on the display, which shows the steps the user has to take to remove air from the venous portion, is called venous air removal window in the present case. The venous air removal window takes the user by the hand and explains the steps to be performed manually and provides the user with appropriate feedback in the form of status reports/a status report after the steps to be performed manually/a step to be performed manually have/has been performed. The manual steps to be performed according to the disclosure are distinguished by their simplicity, so that a user can perform them without prior training/without prior introduction. Finally, the control unit is configured to perform the automatic removal of air from the venous portion when initiated by a user, e.g. by an appropriate input on the user interface.

Advantageous configuration examples are claimed in the dependent claims and are explained in the following.

In addition to the venous hose clamp, a manually actuatable clamp is preferably provided in the venous portion by means of which a user can selectively clamp or release the venous portion.

It is advantageous if the manually actuatable clamp is arranged/provided in the venous portion directly after the dialyzer/downstream of the dialyzer (i.e. at the dialyzer outlet in the venous portion) and thus upstream of the venous hose clamp.

If there is air in the venous portion, the control unit is advantageously configured to indicate an instruction in the venous air removal window to the user that he should close the manually actuatable clamp in the venous portion.

In addition to the combination of automatically performed steps and steps to be performed manually according to the disclosure, the present disclosure is distinguished in particular by the claimed provision of the manually actuatable clamp in addition to the venous hose clamp in the venous portion of the extracorporeal blood circuit. In particular, the manually actuatable clamp allows the steps to be performed manually in a very simple and user-friendly manner.

When there is air in the venous portion, the control unit is preferably configured to display an air-removal button in the venous air removal window, which can be activated by the user by pressing the touch screen. The air-removal button can also be pressed several times or repeatedly (if necessary), for example if there is still air in the venous portion after the air removal process has been performed. Pressing the air-removal button by the user activates the automatic air removal according to the disclosure.

When the control unit detects that the air-removal button has been pressed by the user, it is preferably configured to set a negative pressure in the venous portion and to open the venous hose clamp to suck the air out of the venous portion.

When the control unit detects that the air-removal button has been pressed by the user, it is advantageously configured to check whether the manually actuatable clamp is closed by monitoring a pressure change in the extracorporeal circuit, and to generate an alarm to close the manually actuatable clamp if the manually actuatable clamp is not closed. According to the present disclosure, an alarm to close the manually actuatable clamp is an alarm that notifies a user (optically and/or audibly) that he should close the manually actuatable clamp.

When the control unit detects that the air-removal button has been pressed by the user, it is preferably configured to create a negative pressure, which is less than a predefined value, in a venous air trap located in the venous portion by operating/activating a gauge/level control pump, and subsequently to open the venous hose clamp to automatically sucking out the air from the venous portion. The predefined value is preferably −50 mmHg.

When the control unit is configured to detect that air has been sucked out of the venous portion, it is preferably configured to close the venous hose clamp again and to indicate in the venous air removal window that the removal of air is complete.

When the control unit detects that the removal of air is complete, it is advantageous if it is configured to display a prompt in the venous air removal window telling the user to open the manually actuatable clamp again.

When the user has confirmed on the touch screen that he opened the manually actuatable clamp and the control unit receives the information from the air detector that there is no more air in the venous portion, the control unit is preferably configured to resume a therapy.

Furthermore, it is advantageous if the control unit is configured to check whether the manually actuatable clamp is actually open after a resumption of the (blood treatment) therapy by monitoring a pressure change in the extracorporeal circuit, and if the manually actuatable clamp is still closed, to generate an alarm to open the manually actuatable clamp. According to the present disclosure, an alarm for opening the manually actuatable clamp is an alarm that notifies a user (optically and/or acoustically) that he should open the manually actuatable clamp.

It is practical if the extracorporeal blood circuit and the dialysis fluid circuit are designed as disposable tubes, which are attached to an interface provided on the dialysis device.

Preferably, the blood treatment device has a weighing device, in particular a load cell, for measuring the weight of a bag, in particular a disposable bag containing a fluid required for blood treatment.

Preferably, in addition to the blood pump, the plurality of pumps includes at least a substitution solution pump, a syringe pump, and an effluent pump.

Furthermore, the blood treatment device is preferably equipped with a bar code reader, which is configured to read bar codes on disposable items such as disposable tubing or their packaging.

The blood treatment device is preferably configured for wired communication.

The control unit of the blood treatment device is preferably designed as at least one processor, preferably several processors.

In other words, the disclosure relates to a dialysis device. The dialysis device includes a bar code reader. Furthermore, the dialysis device contains a user interface or a display with a touch screen. The dialysis device also has an interface for a disposable tubing set containing a blood side and a dialysis-fluid side separated by a (semi)permeable membrane for filtering blood (using a dialysis fluid solution/dialysis solution). A substitution solution/replacement solution is supplied to the blood side before/after a dialyzer. The dialysis device has a blood pump, a syringe pump, an effluent pump, a substitution solution pump etc. The dialysis device is configured for wired communication/has wired or wire-connected communication facilities. The dialysis device is characterized by a software that is particularly suitable for use in continuous dialysis therapies, such as renal replacement therapy. The software runs on a large number of processors within the dialysis device. The dialysis device also has an energy management device (integrated circuit). The dialysis device also contains weighing devices, in particular load cells, which measure the weight of disposable bags containing the fluids (e.g. dialysis fluid solution, substitution solution) required for the dialysis therapy.

The control unit of the present disclosure provides an automatic removal of air. If air is present in a venous portion of an extracorporeal blood circuit, this is generally a dangerous situation for a patient. The dialysis device according to the disclosure (in particular its control unit) continuously/permanently monitors the venous portion of the extracorporeal blood circuit with a (safety) air detector in the venous portion. When the 'air in the venous portion' alarm occurs, the venous air removal window appears on the user interface.

When air is detected in the venous portion, the dialysis device stops the blood pump, closes the venous hose clamp, generates a corresponding alarm, and displays the 'air removal from venous portion' window. A user is prompted on the window to close a manually actuatable clamp on the venous portion. This clamp preferably has a specific color, for example blue, and the user is accordingly prompted to close the clamp with the specific color, for example the blue clamp. The 'air removal from venous portion' window also prompts the user to press an air-removal button. When the air-removal button is pressed by the user, the dialysis device (its control unit) reduces the pressure in the venous portion to a negative pressure of preferably −50 mmHg by controlling an air pump (a gauge/level control pump). This air pump is preferably connected to a distributor and it is controlled by a plurality of valves at which point of the disposable hose set the air pump adds air or at which point of the disposable hose set the air pump removes air in order to adjust/reduce the pressure in the venous portion accordingly. Then the dialysis device (its control unit) opens the venous hose clamp and sucks out the air. Afterwards the dialysis device closes the venous hose clamp again. The user can subsequently examine the venous portion. If necessary, he can press the air-removal button again. When the air is removed, the user opens the manually operated (blue) clamp on the venous portion and presses an ok button to resume the blood treatment therapy. The dialysis device resumes the therapy when no more air is detected in the venous portion.

BRIEF DESCRIPTION OF THE DRAWING FIGURES

Figure 2:
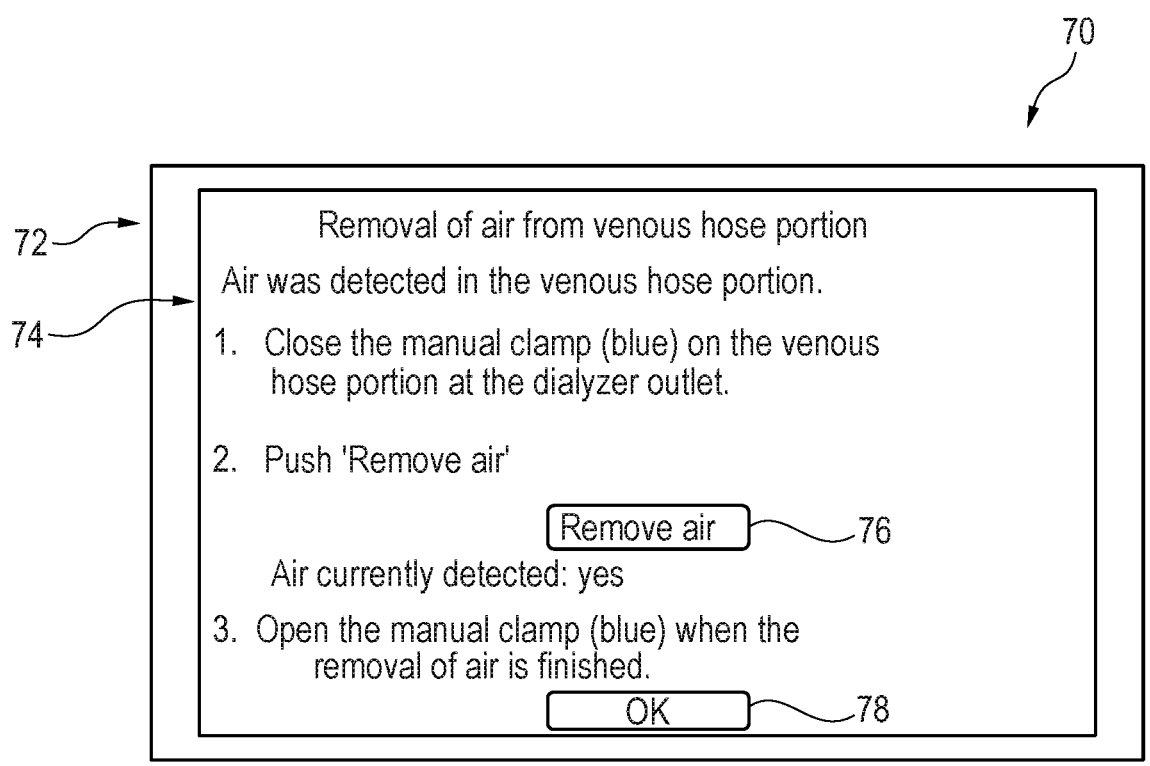

The disclosure is further explained in conjunction with the drawing figures, of which:

FIG. 1 is a schematic view of a blood treatment device according to the present disclosure; and FIG. 2 is a venous air removal window according to the present disclosure.

DETAILED DESCRIPTION

The figures are merely schematic in nature and serve exclusively for understanding the present disclosure. The same elements are marked with the same reference signs.

FIG. 1 shows a schematic view of an extracorporeal blood treatment device (dialysis device) 2. The blood treatment device 2 is basically configured to be used in both continuous and intermittent blood treatment therapies, in particular renal replacement therapies. The blood treatment device 2 is configured in particular as an acute dialysis machine or an acute dialysis device and is thus essentially prepared for use in intensive care units with predominantly unstable patients. With the blood treatment device 2 of the present disclosure, principally a variety of different blood treatment therapies can be performed (e.g. slow continuous ultrafiltration (SCUF), continuous veno-venous hemofiltration (CVVH), continuous veno-venous hemodialysis (CVVHD), continuous veno-venous hemodiafiltration (CVVHDF), therapeutic plasma exchange (TPE), etc.) as well as dilution modes (e.g., pre-dilution, post-dilution, pre-dilution and post-dilution) and anticoagulation types (e.g., none, heparin, citrate, etc.).

The blood treatment device 2 basically has an extracorporeal circuit 4, a dialyzer (hemofilter) 6 and a dialysis fluid circuit 8. The extracorporeal circuit 4 and the dialysis fluid circuit 8 are separated by a membrane 10 provided in the dialyzer 6, through which blood can be filtered using a dialysis fluid solution or without using a dialysis fluid solution.

The extracorporeal circuit 4 comprises an arterial portion 12 and a venous portion 14. In principle, it is provided that the arterial portion 12, in particular one end thereof, is to be connected or attached to an artery of a patient, in particular an intensive care patient. It is also provided that the venous portion 14, in particular one end thereof, is to be connected or attached to a vein of a patient, in particular an intensive care patient.

The arterial portion 12 has, starting from an arterial end 16 in a blood flow direction towards the dialyzer 6, an arterial pressure sensor 18, an (arterial) blood pump 20, and a dialyzer inlet pressure sensor 22. Starting from the dialyzer 6 (a dialyzer outlet 23) in a blood flow direction towards a venous end 24, the venous portion 14 has a manually actuatable clamp 25, a venous expansion chamber or air trap 26, a safety air detector/air detector 28 and a venous hose clamp 30. By means of the manually actuatable clamp 25, a user can selectively clamp off the venous portion 14 or release it. A venous pressure can be measured on/behind the venous expansion chamber 26 using a venous pressure sensor 32. A level/gauge control pump 33, which is provided behind the venous pressure sensor 32, can press air into the venous expansion chamber or air trap 26 or extract air from it and is therefore basically configured and provided to create a negative pressure or an overpressure in the venous expansion chamber or air trap 26 and thus in the venous portion 14.

As shown in FIG. 1, the venous expansion chamber 26 is connected to a substitution solution bag/container 34. A substitution solution pump 36 is provided and configured to pump a substitution solution from the substitution solution bag 34 into the extracorporeal blood circuit 4, in particular into the venous portion 14 thereof (into the venous expansion chamber 26).

The dialysis fluid circuit 8 has at least one outlet 38 for effluent/used dialysis fluid (dialysate)/another fluid. In principle, the effluent/dialysate/the other liquid can flow through the outlet 38 from the dialyzer 6 to a collecting bag/container 40 for effluent/dialysate/etc. In the outlet 38, an effluent pressure sensor 42, a blood leak detector 44 and an effluent pump 46 are arranged or provided in a direction of flow from the dialyzer 6 to the collecting bag 40.

As can be further seen in FIG. 1, a further bag/container 48 is provided in addition to the substitution solution bag 34 and the collecting bag 40. Depending on the desired blood treatment therapy to be performed, the bag 48 may contain, for example, a substitution solution/fluid or a dialysis fluid.

When, for example, a hemodialysis/hemodiafiltration treatment etc. is to be carried out with the extracorporeal blood treatment device 2, i.e. a blood treatment therapy in which dialysis fluid flows through the dialyzer 6 and thus a substance transport from the extracorporeal circuit 4 to the dialysis fluid circuit 8 takes place both by diffusion and convection, then the bag 48 contains dialysis fluid. When a first valve 50 is now opened and both a second valve 52 and a third valve 54 are closed, then the dialysis fluid can be pumped to the dialyzer 6 via a pump 56. When, for example, hemofiltration etc. is to be performed with the extracorporeal blood treatment device 2, i.e. a blood treatment therapy in which no dialysis fluid flows through the dialyzer 6 and thus substance transport from the extracorporeal circuit 4 to the dialysis fluid circuit 8 takes place only via convection/filtration, the bag 48 can contain a substitution solution. When the first valve 50 and the second valve 52 are closed and the third valve 54 is opened, the substitution solution can be pumped from the bag 48 into the arterial portion 12 of the extracorporeal circuit 4 (pre-dilution). When the first valve 50 and the third valve 54 are closed and the second valve 52 is opened, the substitution solution can be pumped from the bag 48 into the venous portion 14 of the extracorporeal circuit 4 (post-dilution). When the first valve 50 is closed and the second valve 52 and the third valve 54 are opened, the substitution solution can be pumped from the bag 48 into both the arterial portion 12 and the venous portion 14 of the extracorporeal circuit (pre-dilution and post-dilution). According to the present disclosure, pre-dilution and post-dilution can also be achieved by pumping the substitution solution from the substitution solution bag 34 via the substitution solution pump 36 into the venous portion 14 of the extracorporeal circuit 4 (post-dilution) and simultaneously pumping the substitution solution from the bag 48 via the pump (substitution solution pump) 56 into the arterial portion 12 of the extracorporeal circuit 4 (pre-dilution).

As shown in FIG. 1, a fluid warmer 58 and a pressure sensor 60 are provided between the pump 56 and the valve assembly consisting of the first valve 50, the second valve 52, and the third valve 54.

The three bags, i.e. the substitution solution bag 34, the collecting bag 40 and the bag 48, each have load cells attached to them, namely a first load cell 62, a second load cell 64 and a third load cell 66. The first load cell 62 is basically configured to measure or monitor the weight of the substitution solution bag 34. The second load cell 64 is basically configured to measure or monitor the weight of the collecting bag 40. The third load cell 66 is basically configured to measure or monitor the weight of the bag 48.

The extracorporeal blood treatment device 2 furthermore has a control unit (CPU) 68, which receives information from the sensors provided in the blood treatment device 2 and which controls the actuators provided in the blood treatment device 2. According to the disclosure, this provides software-supported therapy in particular. The control unit 68 receives in particular information from the arterial pressure sensor 18, the dialyzer inlet pressure sensor 22, the safety air detector 28, the venous pressure sensor 32, the effluent pressure sensor 42, the blood leak detector 44, the pressure sensor 60, the first load cell 62, the second load cell 64, the third load cell 66, etc. The control unit 68 controls in particular the blood pump 20, the venous hose clamp 30, the level/gauge control pump 33, the substitution solution pump 36, the effluent pump 46, the first valve 50, the second valve 52, the third valve 54, the pump 56, the fluid warmer 58, etc. Furthermore, the control unit 68 exchanges information with a user interface 70 designed as a display with touch screen. For example, the control unit 68 may be configured to display information on the user interface 70. Furthermore, input by a user/operator on the user interface 70 can be transferred to the control unit 68.

The control unit 68 of the present disclosure basically receives information from the safety air detector 28, which is located in the venous portion 14 of an extracorporeal (blood) circuit 4. When air is detected by the safety air detector 28, the control unit 68 stops the (arterial) blood pump 20 (preferably all pumps, i.e. not only the arterial blood pump 20 but also the substitution solution pump 36, the effluent pump 46, and the pump 56), closes the venous hose clamp 30, generates an alarm and displays a venous air removal window 74 on a display 72 of the user interface 70.

FIG. 2 shows the venous air removal window 74. The window informs the user that air has been registered/detected in the venous portion 14 of the extracorporeal circuit 4. In a first step, the user is asked to close a manually actuatable (blue) clamp 25 on the venous portion 14, which is located near/at the dialyzer outlet 23 of the dialyzer 6 of the extracorporeal blood treatment device 2.

In a second step, the user is prompted on the venous air removal window 74 to press an air-removal button 76. When the air-removal button 76 is pressed by the user, the control unit 68 checks whether the manually actuatable clamp 25 is actually closed, by monitoring a pressure change in the extracorporeal circuit 4, in particular in its venous portion 14, by means of the venous pressure sensor 32. If the control unit 68 determines that the manually actuatable clamp 25 is not closed, the control unit 68 generates an alarm (acoustic and/or optical), which informs the user that he has to close the manually actuatable clamp 25.

When the control unit 68 determines that the manually actuatable clamp 25 is closed, the control unit 68 of the blood treatment device 2 reduces the pressure in the venous portion 14, in particular in the venous expansion chamber/air trap 26, to a low/negative pressure which is less than a predefined value (preferably −50 mmHg) by controlling the gauge/level control pump 33.

Then the control unit 68 of the blood treatment device 2 opens the venous hose clamp 30, whereby the air is automatically sucked out.

When the control unit 68 detects that the air has been sucked out of the venous portion 14, the control unit 68 closes the venous hose clamp 30 again. The user can then examine the venous portion 14. If necessary, he can press the air-removal button 76 again. When the air has been removed, the venous air removal window 74 indicates this to the user and gives him a status report on the removal of the air. In a third step, the user can open the manually operated (blue) clamp 25 on the venous portion 14 and press an ok button 78 to resume the blood treatment therapy. The blood treatment device 2 will resume therapy when no more air is detected in the venous portion 14 by the safety air detector 28.

After resuming the blood treatment therapy, the control unit 68 checks whether the manually actuatable clamp 25 is actually open. For this purpose, the control unit 68 monitors a pressure change in the venous portion 14 of the extracorporeal circuit 4, which is detected by the venous pressure sensor 32. If the manually actuatable clamp 25 is still closed, the control unit 68 generates an alarm (acoustic and/or optical), which indicates to the user that he should open the manually actuatable clamp 25.

What is claimed:

1. A blood treatment device for use in blood treatment therapies, comprising:
   an extracorporeal blood circuit, a dialyzer with a dialyzer outlet, and a dialysis fluid circuit, wherein the extracorporeal blood circuit and the dialysis fluid circuit are separated from each other via a membrane provided in the dialyzer, via which blood can be filtered, and the extracorporeal blood circuit has an arterial portion upstream of the dialyzer and a venous portion downstream of the dialyzer;
   an air detector arranged in the venous portion and configured to continuously monitor whether air is present in the venous portion;
   a plurality of pumps, including at least one blood pump which is a pump in the arterial portion and is configured to pump blood through the extracorporeal blood circuit;
   a venous hose clamp, which is a hose clamp in the venous portion and is configured to selectively clamp or release the venous portion;
   a user interface comprising a display with a touch screen; and
   a control unit, which is configured, when it receives information from the air detector that there is air in the venous portion, to stop the at least one blood pump, to close the venous hose clamp, to raise an alarm, and to display on the display a venous air removal window displaying instructions to a user for removing air in the venous portion and displaying status reports about removal of air,
   the control unit further configured to carry out an automatic removal of air from the venous portion on a user-initiated basis,
   wherein a manually actuatable clamp is provided in the venous portion in addition to the venous hose clamp, by which a user can selectively clamp or release the venous portion, and
   wherein the control unit is configured, when there is air in the venous portion, to display in the venous air removal window an instruction for the user to close the manually actuatable clamp in the venous portion.

2. The blood treatment device according to claim 1, wherein the manually actuatable clamp is arranged at the dialyzer outlet in the venous portion and thus upstream of the venous hose clamp.

3. The blood treatment device according to claim 1, wherein the control unit is configured, when there is air in the venous portion, to display in the venous air removal window an air-removal button which is actuatable by the user by pressing the touch screen.

4. The blood treatment device according to claim 3, wherein the control unit is configured, when it detects that the air-removal button has been pressed by the user, to check whether the manually actuatable clamp is closed by monitoring a pressure change in the extracorporeal blood circuit, and to generate an alarm to close the manually actuatable clamp if the manually actuatable clamp is not closed.

5. The blood treatment device according to claim 3, wherein the control unit is configured, when it detects that the air-removal button has been pressed by the user, to generate a negative pressure, which is less than a predefined value, in a venous air trap arranged in the venous portion by operating a gauge/level control pump and then to open the venous hose clamp to automatically suck out air from the venous portion.

6. The blood treatment device according to claim 5, wherein the predefined value is −50 mmHg.

7. The blood treatment device according to claim 5, wherein the control unit is configured, when it detects that air has been sucked out of the venous portion, to close the venous hose clamp again and to indicate in the venous air removal window that removal of air is complete.

8. The blood treatment device according to claim 7, wherein the control unit is configured, when it detects that removal of air is complete, to display in the venous air removal window a prompt to the user to open the manually actuatable clamp again.

9. The blood treatment device according to claim 8, wherein the control unit is configured to resume a blood treatment therapy when the user has confirmed on the touch screen that he has opened the manually actuatable clamp, and the control unit receives the information from the air detector that there is no more air in the venous portion.

10. The blood treatment device according to claim 9, wherein the control unit is configured:
  to check whether the manually actuatable clamp is actually open after a resumption of the blood treatment therapy by monitoring a change in pressure in the extracorporeal blood circuit; and
  if the manually actuatable clamp is still closed, to generate an alarm to open the manually actuatable clamp.

11. A blood treatment device for use in blood treatment therapies, comprising:
  an extracorporeal blood circuit, a dialyzer with a dialyzer outlet, and a dialysis fluid circuit, wherein the extracorporeal blood circuit and the dialysis fluid circuit are separated from each other via a membrane provided in the dialyzer, via which blood can be filtered, and the extracorporeal blood circuit has an arterial portion upstream of the dialyzer and a venous portion downstream of the dialyzer;
  an air detector arranged in the venous portion and configured to continuously monitor whether air is present in the venous portion;
  a plurality of pumps, including at least one blood pump which is a pump in the arterial portion and is configured to pump blood through the extracorporeal blood circuit;
  a venous hose clamp, which is a hose clamp in the venous portion and is configured to selectively clamp or release the venous portion;
  a user interface comprising a display with a touch screen; and
  a control unit, which is configured, when it receives information from the air detector that there is air in the venous portion, to stop the at least one blood pump, to close the venous hose clamp, to raise an alarm, and to display on the display a venous air removal window displaying instructions to a user for removing air in the venous portion and displaying status reports about removal of air,
  the control unit further configured to carry out an automatic removal of air from the venous portion on a user-initiated basis,
  wherein a manually actuatable clamp is provided in the venous portion in addition to the venous hose clamp, by which a user can selectively clamp or release the venous portion, and
  wherein the manually actuatable clamp is arranged at the dialyzer outlet in the venous portion and thus upstream of the venous hose clamp.

* * * * *